United States Patent [19]

Carcia et al.

[11] Patent Number: 4,474,996
[45] Date of Patent: Oct. 2, 1984

[54] PRODUCTION OF FORMALDEHYDE

[75] Inventors: Peter F. Carcia; Velliyur Nott M. Rao, both of Wilmington, Del.

[73] Assignee: E. I. Du Pont de Nemours and Company, Wilmington, Del.

[21] Appl. No.: 475,033

[22] Filed: Mar. 14, 1983

[51] Int. Cl.³ .............................................. C07C 45/37
[52] U.S. Cl. .................................... 568/473; 568/471; 568/472
[58] Field of Search ........................ 568/473, 471, 472

[56] References Cited

U.S. PATENT DOCUMENTS

| | | | |
|---|---|---|---|
| 2,462,413 | 2/1949 | Meath | 568/473 |
| 3,959,383 | 5/1976 | Northheimer | 568/473 |
| 4,046,712 | 9/1977 | Cairns et al. | 252/447 |
| 4,167,527 | 9/1979 | Nielson | 568/473 |

FOREIGN PATENT DOCUMENTS

| | | | |
|---|---|---|---|
| 1455248 | 11/1976 | United Kingdom | 252/447 |
| 1537839 | 1/1979 | United Kingdom | 252/447 |

OTHER PUBLICATIONS

S. K. Sharma & J. Spitz, Thin Solid Films, 61, L 13–15 (1979).
A. E. Presland et al., Progress in Surface Science, 3, pp. 63–96 (1973).
B, Abeles et al., Advanced Physics, 24, pp. 407–459 (1975).

Primary Examiner—Werren B. Lone

[57] ABSTRACT

Methanol is converted to formaldehyde by oxidative dehydrogenation using as catalyst sputtered or ion plated silver or silver/gold alloy on an inert hard, non-porous support.

6 Claims, No Drawings

PRODUCTION OF FORMALDEHYDE

BACKGROUND OF THE INVENTION

1. Field of the Invention

This invention is concerned with an improvement in the production of formaldehyde from methanol. In particular, it relates to such a process where the catalyst is a supported silver catalyst prepared by ion plating or RF sputtering.

2. Prior Art

The catalytic converion of methanol to produce formaldehyde has been known since 1878. The use of silver catalysts for such a process has been known since at least 1908 and is disclosed in German Pat. No. 228,687. Other metals or metal alloys as well as metal oxides have also been suggested and used for this process.

Commercially there are two processes that are in widespread use. The first utilizes silver as the catalyst. This process is carried out in a methanol rich atmosphere. The second uses a metal oxide catalyst and operates in an oxygen-rich atmosphere. Basically the first process is operated at approximately one to three atmospheres absolute, although other pressure ranges can be employed if desired. Methanol and air are passed over a stationary bed of the catalyst. The overall reaction is exothermic in nature and can operate anywhere between 450°–750° C. depending upon process and product requirements. The mixture which is passed through the catalyst bed is not restricted to methanol and air only since various diluents have been disclosed in the literature. Diluents may consist of steam, carbon oxides and recycled off gases, including formaldehyde.

The mechanism of formaldehyde production is believed to be a combinaton of two reactions, namely the dehydrogenation and oxidative dehydrogenation of methanol.

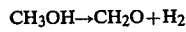

$$CH_3OH \rightarrow CH_2O + H_2$$

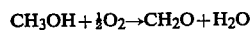

$$CH_3OH + \tfrac{1}{2}O_2 \rightarrow CH_2O + H_2O$$

Depending upon the conversion required, the silver catalyzed process can be operated in stages. Single stage operation allows only moderate amounts of methanol to be converted in a single pass limited by reaction temperature unless a heat sink such as inerts or water is employed. This necessitates distillation of unreacted methanol from the product formaldehyde and entails substantial investment in distillation facilities.

Another way to operate the process which eliminates distillation or other concentration facilities is to use two or more catalytic stages with interstage cooling. A basic two-stage process is disclosed in U.S. Pat. No. 2,462,413 to Meath. An improvement over the Meath process where even lower amounts of methanol in the product can be obtained is disclosed in U.S. Pat. No. 3,959,383 issued to Northheimer.

SUMMARY OF THE INVENTION

The present invention relates to an improved process of oxidatively dehydrogenating methanol to form formaldehyde over a silver or silver/gold catalyst wherein the metal/metals is sputtered or ion plated on an inert support. Such catalysts give a higher productivity of formaldehyde. When measured as g of product/g of silver/hr, productivity increases by more than a factor of 50 as compared with conventional silver crystal or silver wool catalysts.

DETAILED DESCRIPTION

The catalyst used in the present invention is sputtered or ion plated silver of silver/gold on an inert support. Generally the metal loading will comprise from 0.5–10 weight percent of the total catalyst composition and preferably from 1–5 weight percent of the total composition. Generally the catalyst support will be a hard, nonporous refractory particulate material having a mean particle diameter in the range of from 0.1 micron to 0.5 centimeter. Generally the support should have a surface area below about 20 square meters per gram and preferably below 2 square meters per gram. Generally the support will be ceramic material. Alumina and silica are the preferred catalyst supports although other oxides such as ceria, yttria, zirconia or titania can be used.

The catalysts of the invention were prepared by physical vapor deposition either by ion plating where evaporated silver was allowed to deposit on a silica support which was biased electrically or by RF sputtering. In the latter method, fused silica particles which pass a 30 mesh (U.S. Sieve Series) screen and are retained on a 50 mesh (U.S. Sieve Series) screen were distributed in several pyrex dishes on a rotating substrate table beneath a silver or silver/gold target and coated with the metal/metals. The particulate substrates were peridically mixed outside the sputtering chamber to ensure uniformity.

A more detailed description of the preparation of the catalyst is disclosed in Ser. No. 475,031, filed on even date herewith.

The terms "conversion" and "selectivity" used in the specification, examples and claims are defined as follows:

$$\text{Conversion, mole \%} = \frac{\text{moles methanol converted}}{\text{moles methanol fed}} \times 100$$

$$\text{Selectivity, moles \%} = \frac{\text{moles formaldehyde produced}}{\text{moles methanol converted}} \times 100$$

In a typical formaldehyde process, using silver or silver gold catalyzed reactors, methanol is fed to a vaporizer then to a superheater where the temperature is raised to from about 140° to about 180° C. The superheated methanol is mixed with air and fed to the reactor which is operated at from 450°–750° C. Optionally the product gases from the reactor can be mixed with additional air and sent to a second reactor to increase conversion of methanol to formaldehyde. The gases finally are sent to an absorber where they are cooled to from 25°–45° C. Product formaldehyde in water, as 40–60% formaldehyde, is removed from the absorber.

The catalysts useful herein are silver or silver gold alloys containing from 25–75 atomic percent silver and the remainder gold.

EXAMPLES

Examples 1–25

A 10 mm (I.D.) quartz tube is filled to a depth of one inch (25.4 mm) with the catalyst reported in Table I which passes a 20 mesh screen and is retained on a 60 mesh screen (Tyler Sieve Series). Methanol, 1.3 g/min, is vaporized and mixed with preheated air to furnish the desired oxygen to methanol ratio reported in Table I and passed through the catalyst bed. The catalyst section is heated externally to initiate reaction and once initiated the external heat is adjusted to maintain the temperature at the value reported in Table I. When water vapor is used in the feed in addition to methanol and air, liquid water is vaporized to give the water to methanol ratios reported in Table I.

The product from the reactor is analyzed by gas chromatography to determine conversion and selectivity. The catalyst used in Examples 17-19 was 4% Ag cosputtered with $SiO_2$ on $SiO_2$. The catalyst used in Example 21 contained 4.5 weight percent metal sputtered on $SiO_2$ and the metal was 60 weight percent Au and 40 weight percent Ag. The catalyst used in Examples 22-25 Ag/$SiO_2$ cosputtered on $SiO_2$ from a disc of a mix of Ag/$SiO_2$ to provide a catalyst containing about 2% Ag.

In Example 26 both quartz tubes were filled with silver crystals as a control catalyst. In Example 27 both quartz tubes were filled with 4 weight percent Ag sputtered on $\alpha Al_2O_3$.

TABLE II

| Example | Bed Temp 1st °C. | Bed Temp 2nd °C. | Mole Ratio $O_2$/MeOH | Overall Conversion MeOH % | Overall Selectivity HCHO % |
|---|---|---|---|---|---|
| 26 | 580 | 635 | 0.435 | 98.6 | 83.8 |
| 27 | 598 | 604 | 0.396 | 97.3 | 84.7 |

We claim:

1. A process of vapor phase oxidative dehydrogenation of methanol in the presence of an oxygen containing gas at from 450° to 750° C. to produce formalde-

TABLE I

| | Catalyst | Bed Temp. °C. | Mole Ratio $O_2$MeOH | Mole Ratio $H_2O$/MeOH | Conversion MeOH % | Selectivity HCHO % |
|---|---|---|---|---|---|---|
| 1. | Silver Crystals (control) | 590 | 0.224 | — | 63.3 | 91.9 |
| 2. | " | 610 | 0.255 | — | 72.9 | 91.5 |
| 3. | " | 634 | 0.279 | — | 79.1 | 91.0 |
| 4. | " | 687 | 0.342 | 0.48 | 89.5 | 90.5 |
| 5. | " | 680 | 0.367 | 0.91 | 92.6 | 89.9 |
| 6. | 1 wt % Ag ion plated on $SiO_2$ | 595 | 0.223 | — | 65.5 | 92.4 |
| 7. | " | 645 | 0.277 | — | 80.0 | 92.6 |
| 8. | " | 662 | 0.303 | 0.27 | 85.0 | 92.5 |
| 9. | " | 690 | 0.333 | 0.55 | 89.0 | 92.1 |
| 10. | " | 695 | 0.356 | 0.84 | 92.0 | 91.3 |
| 11. | 2 wt % Ag sputtered on $SiO_2$ | 619 | 0.251 | — | 75.3 | 90.4 |
| 12. | " | 650 | 0.313 | 0.60 | 87.4 | 90.7 |
| 13. | " | 685 | 0.361 | 1.18 | 92.3 | 89.9 |
| 14. | 4 wt % Ag sputtered on $Al_2O_3$ | 614 | 0.238 | — | 66.5 | 91.7 |
| 15. | " | 652 | 0.282 | 0.60 | 77.2 | 92.0 |
| 16. | " | 722 | 0.349 | 0.84 | 89.8 | 91.2 |
| 17. | 4 wt % Ag cosputtered on $SiO_2$ | 622 | 0.256 | — | 68.5 | 92.8 |
| 18. | " | 670 | 0.329 | 0.51 | 83.6 | 92.2 |
| 19. | " | 698 | 0.389 | 1.11 | 92.6 | 91.3 |
| 20. | Ag/Au 60/40 crystals (control) | 586 | 0.236 | — | 62.4 | 92.5 |
| 21. | Ag/Au sputtered on $SiO_2$ | 608 | 0.254 | — | 75.2 | 91.2 |
| 22. | Ag/$SiO_2$ cosputtered on $SiO_2$ | 663 | 0.280 | — | 68.1 | 92.6 |
| 23. | " | 695 | 0.312 | — | 73.9 | 92.2 |
| 24. | " | 670 | 0.342 | 0.52 | 80.4 | 92.9 |
| 25. | " | 696 | 0.389 | 1.09 | 90.9 | 91.7 |

Examples 26 and 27

Two 10 mm (I.D.) quartz tubes are filled to a depth of one inch (25.4 mm) with the catalyst reported below. The two tubes are connected in series with provision to add air to the effluent from the first tube prior to entering the second tube. The reaction in the first tube is initiated with methanol (1.3 g/min) and air as described for Examples 1-25. The reaction in the second tube is initiated with product from the first reactor and additional air. Both tubes have external heaters around the catalyst section. After reaction is initiated these heaters are adjusted to maintain the values reported for two-stage operation. The product from the second stage is analyzed by gas chromatography to determine conversion and selectivity.

hyde, the improvement that the catalyst is formed of a particulate, hard, nonporous, refractory support containing on its surface from 0.5-10 weight percent silver or silver/gold alloy which has been deposited by physical vapor deposition.

2. The process of claim 1 wherein the silver or silver/gold alloy has been ion plated onto the support.

3. The process of claim 2 wherein the catalyst contains from 1-5 weight percent silver.

4. The process of claim 1 wherein the silver or silver/gold alloy has been sputtered onto the support.

5. The process of claim 4 wherein the catalyst contains from 1-5 weight percent silver or silver/gold alloy.

6. The process of claim 5 wherein the catalyst is formed by cosputtering silver or a silver/gold alloy and silica onto a silica support.

* * * * *